United States Patent [19]
Stekloff

[11] Patent Number: 5,791,476
[45] Date of Patent: *Aug. 11, 1998

[54] PACKAGE CONTAINER FOR VIALS

[76] Inventor: Debra S. Stekloff, 1121 Dunston Dr., St Louis, Mo. 63146

[ * ] Notice: This patent issued on a continued prosecution application filed under 37 CFR 1.53(d), and is subject to the twenty year patent term provisions of 35 U.S.C. 154(a)(2).

[21] Appl. No.: 733,883

[22] Filed: Oct. 18, 1996

[51] Int. Cl.[6] .......................... B65D 81/02; B65D 30/22
[52] U.S. Cl. .......................... 206/521; 206/522; 206/591; 206/594; 383/38; 383/86
[58] Field of Search .......................... 206/446, 366, 206/363, 521, 522, 591, 594; 229/92.8; 383/98, 99, 38, 86, 211

[56] References Cited

U.S. PATENT DOCUMENTS

| | | | |
|---|---|---|---|
| 3,057,471 | 10/1962 | Stonehill et al. | 383/211 |
| 3,616,991 | 11/1971 | Beck | 383/86 |
| 3,743,173 | 7/1973 | Lasker | 206/521 |
| 3,942,713 | 3/1976 | Olson et al. | 383/86 |
| 4,785,940 | 11/1988 | Wilson | 383/211 |
| 4,789,248 | 12/1988 | Penas | 383/38 |
| 5,002,401 | 3/1991 | Blackman | 383/38 |
| 5,102,234 | 4/1992 | Levy | 383/38 |
| 5,167,455 | 12/1992 | Forman | 383/211 |
| 5,533,624 | 7/1996 | Solderholm et al. | 383/86 |
| 5,547,075 | 8/1996 | Hoogerwood | 206/522 |

FOREIGN PATENT DOCUMENTS 2415943  9/1979  France .......................... 206/522

*Primary Examiner*—M. D. Patterson
*Assistant Examiner*—Anthony Stashick
*Attorney, Agent, or Firm*—Haverstock, Garrett & Roberts

[57] ABSTRACT

A package container is disclosed which is for storing and transporting a blood vial in a secured position, the package container comprises a sheet of thermoplastic material formed into an envelope, a panel of bubble wrap material inserted into the envelope to form a first and a second pocket within the envelope, and a flap having an band of adhesive formed thereon for closing the envelope to close the pockets.

20 Claims, 4 Drawing Sheets

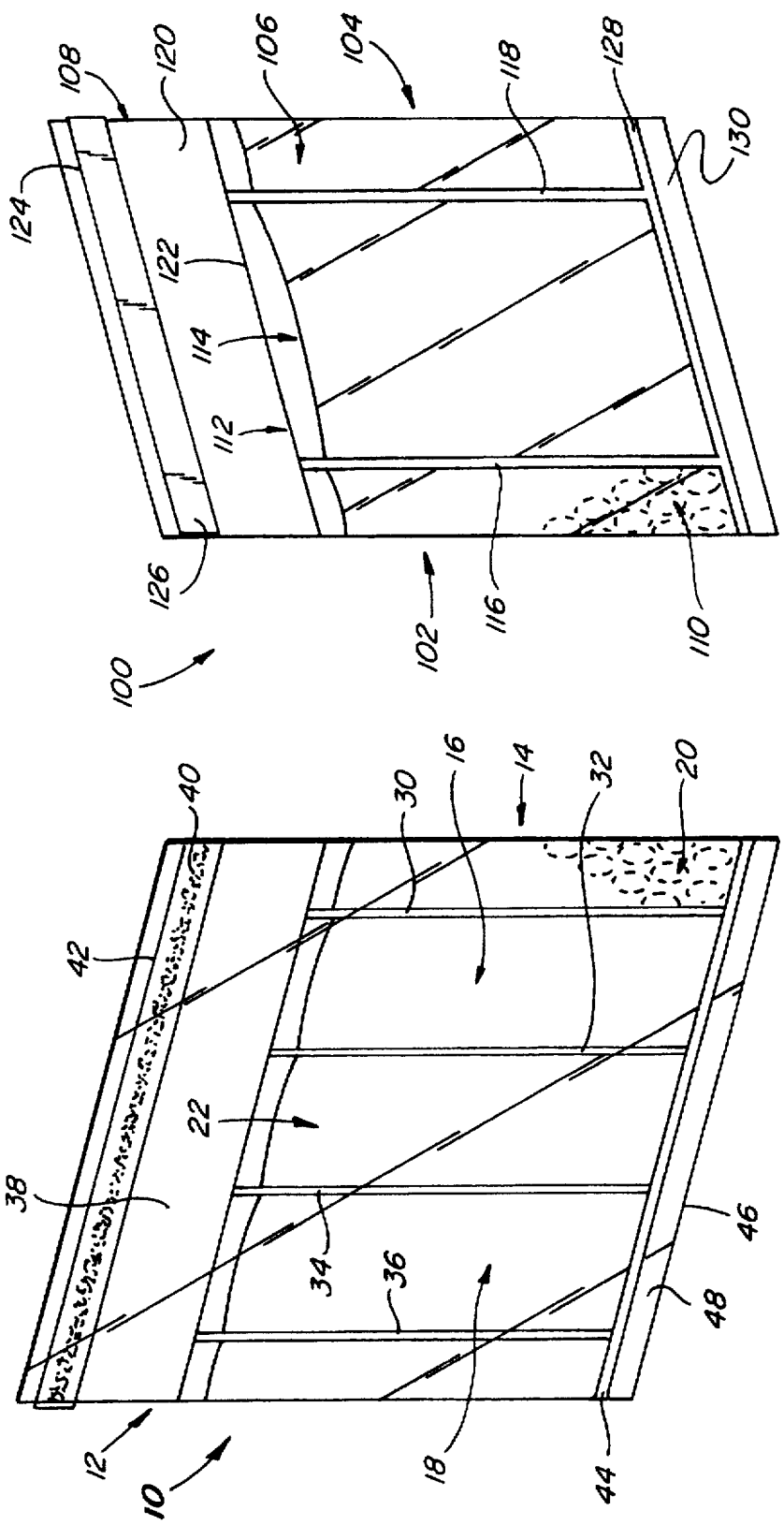

PACKAGE CONTAINER FOR VIALS

BACKGROUND OF THE INVENTION

The present invention relates to a package container for vials and more particularly to a package container for preventing vials inserted therein from breaking during storage or shipping of the vials.

In hospitals a procedure which is handled on a daily basis is the drawing of blood samples from patients for testing purposes. Glass vials are used to both receive and store the blood once it is drawn. The glass vials are then transported to a lab for testing using various methods such as placing the vials in a cart, hand carrying the vials, or by using a pneumatic tube system. When using any of the various transportation methods the vials may be placed in plastic envelopes. Although the envelopes are useful one problem associated with their use is that the glass vials tend to break in the envelopes because the envelopes are flimsy and do not protect the vials from breaking. In the event that the vials do break, blood leaks from the envelopes and the area where the leakage occurred has to be cleaned. In the case where the vial breaks in the pneumatic tubes, the pneumatic tube system has to be completely shut down and the tubes cleaned. Additionally, since the vials break, more blood must be drawn from the patient for testing. What is needed is a package container which can hold the vials and prevent the vials from being broken and still allow the transportation methods in place today to be used.

Another common occurrence in hospitals is the transportation of medications from the pharmacy to the nurses station. Typically such medications, if in liquid form, are stored in glass bottles. Again, during the transportation of such glass bottles breakage occurs and the area wherein the breakage occurred needs to be cleaned. If a glass bottle breaks in the pneumatic tube system, the system has to be shut down and cleaned. Replacement of the medication is also required. A package container which stores glass bottles and prevents the glass bottles from breakage and still permits use of the current transportation modes is needed.

The present invention is designed to obviate and overcome many of the disadvantages and shortcomings experienced with the use of plastic envelopes in transporting and storing vials and to provide a package container which can be easily utilized to transport and store vials. Moreover, since the package container of the present invention is simple to use it offers the advantage that no modifications to any presently used transportation methods or devices are required.

SUMMARY OF THE INVENTION

The present device is a package container for storing and transporting a blood vial in a secured position, the package container comprises a sheet of thermoplastic material formed into an envelope, a panel of bubble wrap material inserted into the envelope to form a first and a second pocket within the envelope, and means for closing the envelope to close the pockets.

Another embodiment of the present invention is a package container for storing and transporting at least one blood vial in a secured position, the package container comprises a sheet of thermoplastic material having a front side and a back side, the sheet being formed into the shape of an envelope, a panel of bubble wrap material inserted into the envelope to form a first pocket between the back side and the panel and a second pocket formed between the front side and the panel, the back side further having a flap portion extending above the envelope with the flap having a band of adhesive and a strip of material covering the band of adhesive, the strip of material being removable from the band of adhesive when the flap is positioned over the front side to close the envelope.

In still another embodiment of the present invention a package container for storing and transporting at least two blood vials in a secured position is disclosed with the package container comprising a sheet of thermoplastic material having a front side and a back side, the sheet being formed into the shape of an envelope, a second sheet of thermoplastic material inserted into the envelope to form a first pocket between the back side and the second sheet of thermoplastic material and a pair of pockets formed between the front side and the second sheet of thermoplastic material, the back side further having a flap portion extending above the envelope with the flap having a band of adhesive and a strip of material covering the band of adhesive, the strip of material being removable from the band of adhesive when the flap is positioned over the front side to close the envelope.

In light of the foregoing comments, it will be recognized that a principal object of the present invention is to provide an improved packaged container for vials or bottles.

A further object of the invention is to provide a package container which is of simple construction and design and which can be easily employed with highly reliable results.

Another object of the present invention is to provide a package container which protects vials during transportation and storage of the vials.

An object of the invention is to provide a package container for vials which protects the vials from breakage during transportation and includes a pocket for storage of identification information of the vials contained in the package container.

Another object of the present invention is to provide a package container which protects glass medication bottles from breakage during storage and transportation.

These and other objects and advantages of the present invention will become apparent after considering the following detailed description in conjunction with the accompanying drawings.

BRIEF DESCRIPTION OF THE DRAWINGS

FIG. 4 is a prespective view of the back of the package container shown in FIG. 1;

FIG. 5 is a perspective view of a second preferred embodiment of a package container constructed according to the present invention;

DETAILED DESCRIPTION OF THE PREFERRED EMBODIMENTS

Figure 1:
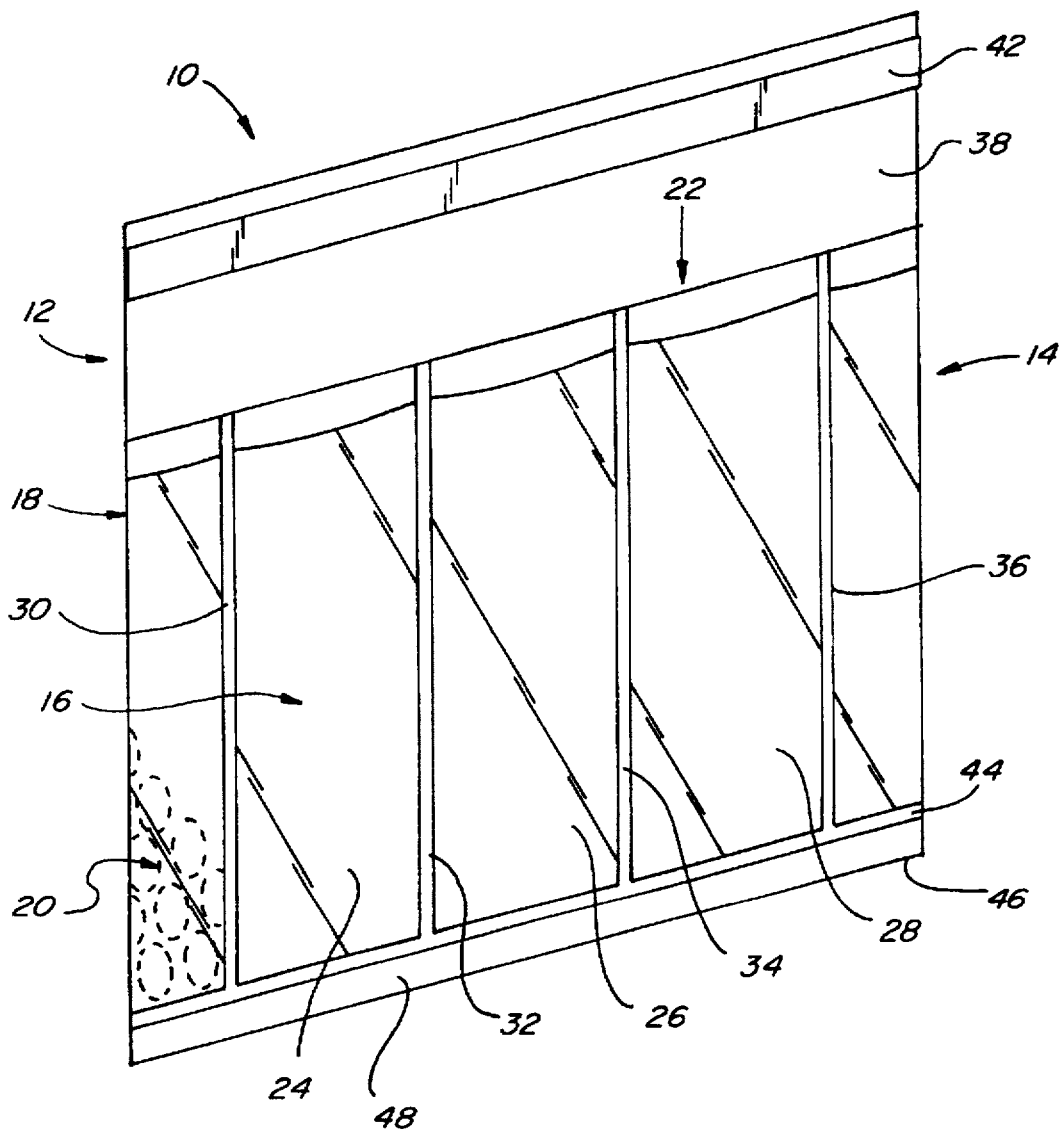
FIG. 1 is a perspective view of a preferred embodiment of a package container constructed according to the present invention.
Figure 3:
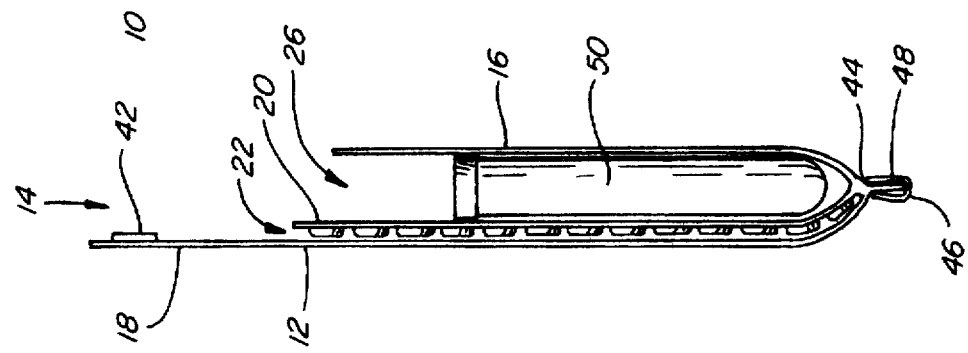
FIG. 3 is a cross sectional view of the package container shown in FIG. 2 taken along the plane of line 2—2.
Figure 2:
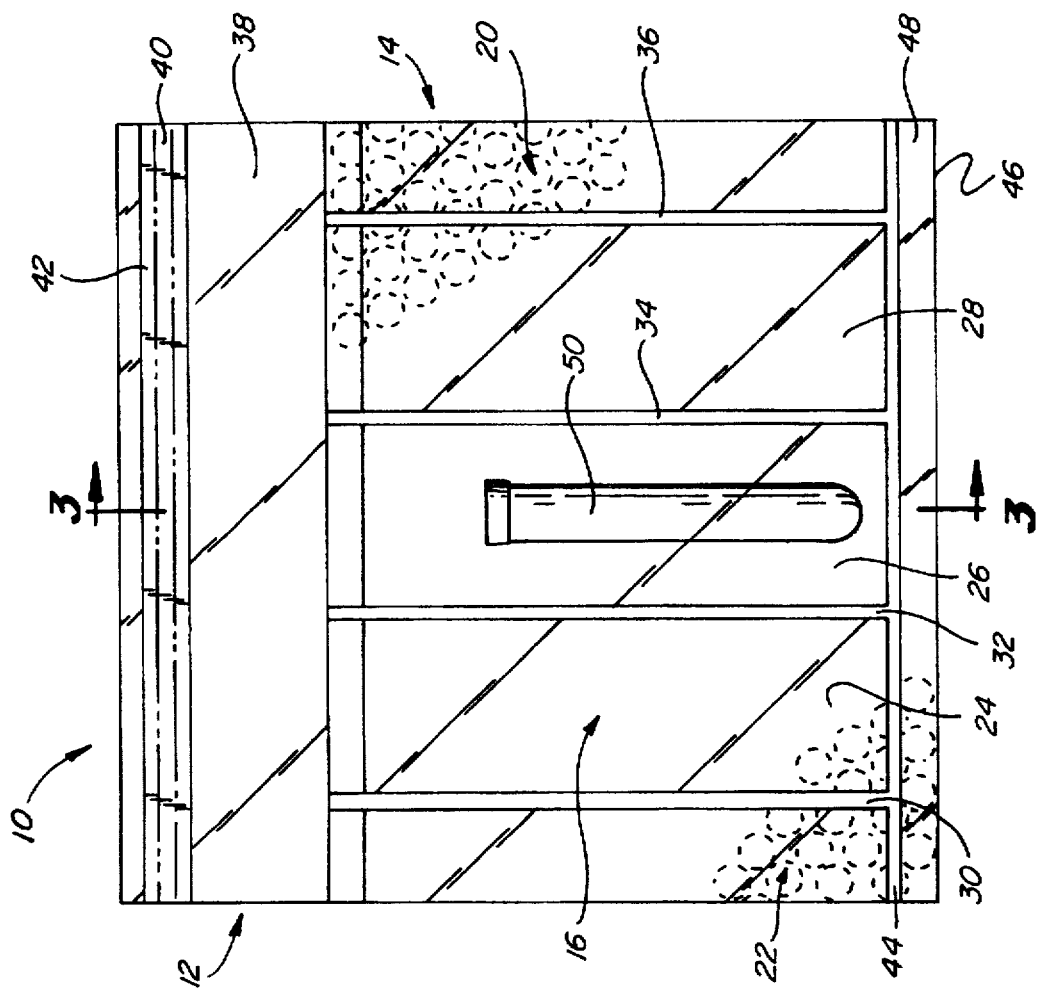
FIG. 2 is a perspective view of the front of the package container shown in FIG. 1.

Referring now to the drawings more particularly by reference numbers, wherein like numbers refer to like items throughout the various drawings, numeral 10 refers to a package container constructed according to the present invention. In FIGS. 1, 2, and 3, the package container 10 comprises a sheet of thermoplastic material 12 which is formed into the shape of an envelope 14 with the envelope 14 having a front side 16 and a back side 18. Examples of a sheet of thermoplastic material are polyethylene or polypropylene and such materials may be clear. A sheet or panel of bubble wrap material 20 is inserted into the envelope 14 to form a first pocket 22 between the sheet of bubble wrap material 20 and the back side 18 of the envelope 14. Three separate pockets 24, 26, and 28 are formed between the sheet of bubble wrap material 20 and the front side 16 of the envelope 14 by fusing the front side 16 to the sheet of bubble wrap material 20 as is shown by fusion lines 30, 32, 34, and 36. In particular, fusion lines 30 and 32 are used to form the pocket 24, fusion lines 32 and 34 form and define the pocket 26, and fusion lines 34 and 36 are used to form the pocket 28. A flap portion 38, which is part of the back side 18, extends above the pockets 22, 24, 26, and 28 of the envelope 14 and includes a band of an adhesive 40 which is covered by a release strip 42. The release strip 42 covers the adhesive 40 until it is to be used. Another fusion line 44 is formed at the bottom 46 of the package container 10 between the bubble wrap 20 and the front side 16 of the envelope 14. The fusion line 44 is perpendicular to the other fusion lines 30, 32, 34, and 36. The fusion line 44 traps a section 48 of the bubble wrap 20 and this acts to provide a cushion below any of the vials which are inserted into any of the pockets 24, 26, and 28 to insure that the bottoms of the vials will be protected from breakage.

The pocket 24 is used to receive and store a first blood vial (not shown), the pocket 26 is used to receive and store a second blood vial 50, and the pocket 28 is used to receive and store a third blood vial (not shown). Typically, three blood samples are drawn from a patient and this is why the three pockets 24, 26, and 28 have been formed in the container 10. Although the three pockets 24, 26, and 28 are shown with respect to the package container 10, it is to be understood that it is also possible and contemplated to have more or less pockets depending upon the particular situation. For example, some hospitals may require that five blood samples be drawn from patients and therefore a package container having five pockets will be required. The first pocket 22 is used to receive a paper form which has written thereon patient identification information and other information for the laboratory. Once the vials and the form have been placed in the envelope 14, the strip of material 42 is removed from the band of adhesive 40 and the flap 38 is folded over so that the adhesive 40 contacts the front side 16 of the envelope 14 to close the envelope 14. Once closed, the container 10 is used to store and transport the blood vials in a safe manner. The bubble wrap material 20 acts to protect the vials within the pockets 24, 26, and 28 from breakage during storage and transportation. Additionally, the band of adhesive 40 may be of the type which is releasable from the front side 16 of the envelope 14 so that the package container 10 may be reusable if desired.

Referring now in particular to FIG. 3, a cross-sectional view of the package container 10 is shown. The package container 10 has the bubble wrap material 20 inserted into the envelope 14. Pocket 26 is best illustrated and is shown formed between the panel of bubble wrap material 20 and the front side 16. Pocket 22 is also shown being defined by the back side 18 and the panel 20.

The back side 18 of the package container is depicted in FIG. 4. The back side 18 is shown to include the flap portion 38 having the band of adhesive 40 which is covered by the release strip 42. The pocket 22 is provided to receive an identification form or any other paper work which is required to identify the contents of the package container 10.

FIG. 5 illustrates a second embodiment of a package container 100 constructed according to the present invention. The package container 100 comprises a sheet of thermoplastic material 102 which has been formed into the shape of an envelope 104 with the envelope 104 having a front side 106 and a back side 108. A sheet of bubble wrap material 110 is inserted into the envelope 104 to form a first pocket 112 between the sheet of bubble wrap material 110 and the back side 108 of the envelope 104. A second pocket 114 is formed between the sheet of bubble wrap material 110 and the front side 106 of the envelope 104 by fusing the front side 106 to the sheet of bubble wrap material 110 as is shown by fusion lines 116 and 118. A flap 120 extends above an opening 122 of the envelope 104 and includes a band of an adhesive 124 which is covered by a strip of material 126. The second pocket 114 is used to receive and store a medicine bottle (not shown), such as the type where liquid medication is stored. The first pocket 112 is used to receive a form which identifies the medicine bottle stored therein. Once the medicine bottle and the form have been placed in the envelope 104, the strip of material 126 is removed from the band of adhesive 124 and the flap 120 is folded over so that the adhesive 124 contacts the front side 106 of the envelope 104 to close the opening 122 of the envelope 104. Once closed, the container 100 is used to store and transport the medicine bottle in a safe manner. The bubble wrap material 110 acts to protect the bottle inserted within the second pocket 114 from breakage during storage and transportation. Additionally, the band of adhesive 124 may be of the type which is releasable from the front side 106 of the envelope 104 so that the package container 100 is reusable. Another fusion line 128 is formed between the bubble wrap 110 and the front side 106 of the envelope 104 which is perpendicular to the fusion lines 116 and 118. The fusion line 128 provides a section 130 of the bubble wrap 110 below the medicine bottle to insure that the bottom of the medicine bottle will be protected from breakage during storage and/or transportation.

Figure 6:
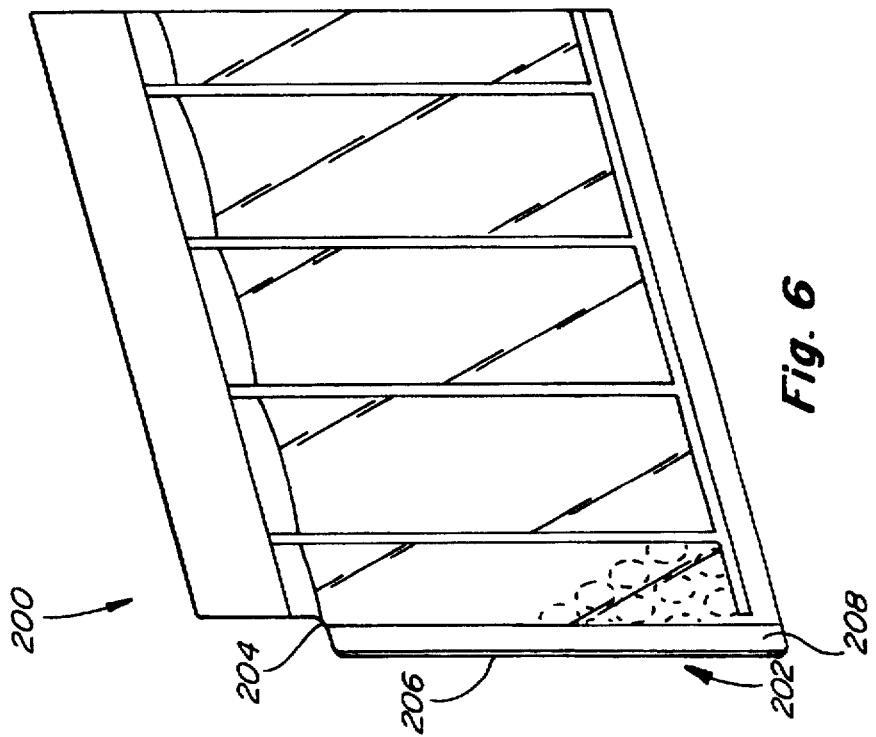
FIG. 6 is a perspective view of a third preferred embodiment of a package container constructed according to the present invention.

With reference now to FIG. 6, a third embodiment of a package container 200 constructed according to the present invention is illustrated. The package container 200 is similar to the package container 10 with the principal difference being a second flap 202 of thermoplastic material being positioned along a side 204 of the package container 200. The second flap 202 may extend along the entire side 204 or only a portion of the side 204. The second flap 202 further includes a band of adhesive 206 which is covered by a strip of material 208. The package container 200 may be rolled up and the flap 202 is provided to adhere the rolled up package container 200 in place. The adhesive 206 may be of the type that is releasable so that the package container 200 may be reusable. It is further contemplated that a similar flap may be incorporated with the package container 100 shown in FIG. 5.

Figure 7:
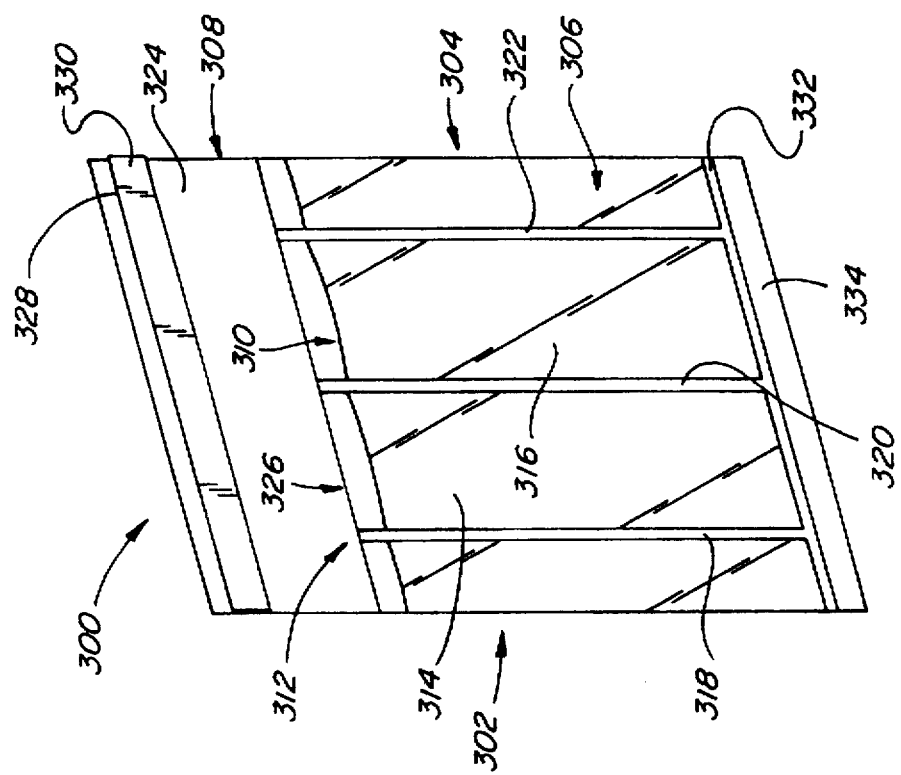
FIG. 7 is a perspective view of a fourth preferred embodiment of a package container constructed according to the present invention.

FIG. 7 illustrates a fourth embodiment of a package container 300 constructed according to the present invention. The package container 300 comprises a sheet of thermoplastic material 302 which has been formed into the shape of an envelope 304 with the envelope 304 having a front side 306 and a back side 308. A second sheet of thermoplastic material 310 is inserted into the envelope 304 to form a first pocket 312 between the second sheet of thermoplastic material 310 and the back side 308 of the envelope 304. Two separate pockets 314 and 316 are formed between the second sheet of thermoplastic material 310 and the front side 306 of the envelope 304 by fusing the front side 306 to the second sheet of thermoplastic material 310 as is shown by fusion lines 318, 320, and 322. A flap 324 extends above an opening 326 of the envelope 304 and includes a band of an adhesive 328 which is covered by a strip of material 330. The pockets 314 and 316 are used to receive and store blood vials (not shown). The first pocket 312 is used to receive a form which identifies the vials stored therein. Once the vials and the form have been placed in the envelope 304, the strip of material 330 is removed from the band of adhesive 328 and the flap 324 is folded over so that the adhesive 328 contacts the front side 306 of the envelope 304 to close the opening 326 of the envelope 304. Once closed, the container 300 is used to store and transport the vials in a safe manner. The second sheet of thermoplastic material 310 acts to protect the vials inserted within the pockets 314 and 316 from breaking during storage and transportation. Additionally, the band of adhesive 328 may be of the type which is releasable from the front side 306 of the envelope 304 so that the package container 300 is reusable. Another fusion line 332 is formed between the second sheet of thermoplastic material 310 and the front side 306 of the envelope 304 which is perpendicular to the fusion lines 318, 320, and 322. The fusion line 332 provides a section 334 of the second sheet of thermoplastic material 310 below the vials to insure that the bottoms of the vials will be protected from breakage during storage and/or transportation. The package container 300 may also be constructed to include a second flap similar to the second flap 202 which is shown in reference to FIG. 6.

Although the package containers 10, 100, 200, and 300 have been shown constructed of a single sheet of thermoplastic material it is also possible to construct the envelope portion by using two sheets of thermoplastic material with a front sheet and a back sheet. The back sheet may have a length that is greater than the front sheet with the greater length forming the flap to be folded over. The front sheet and the back sheet each having a bottom edge, a pair of side edges, and a top edge. The bottom edges and the si de edges of the front sheet and the back sheet may be fused or adhered together to form the envelope. Additionally, the package containers 10, 150, and 200 may be constructed of a single sheet or two sheets of bubble wrap material which may be used to form the envelope portion of the package containers 10, 100, and 200. With the envelope portion formed from the bubble wrap material a sheet of thermoplastic material may be adhered to the envelope to form the pocket in which the identification form is inserted and the flap portion.

Additionally, the construction of the package containers 10, 100, and 200 may also be accomplished by forming the envelope shape at the same time the panel of bubble wrap material is inserted into the envelope so that the panel and the envelope are formed as one unitary piece. The pockets, for example 24, 26, and 28 may be formed after the envelope and the panel are fused together.

Thus there has been shown and described several embodiments of novel package containers which embodiments fulfill all of the objects and advantages sought therefor. It will be apparent to those skilled in the art, however, that many changes, modifications, variations, and other uses and applications for the subject device are possible. All such changes, modifications, variations, and other uses and applications which do not depart from the spirit and scope of the invention are deemed to be covered by the invention which is limited only by the claims which follow.

What is claimed is:

1. A package container for storing and transporting a blood vial in a secured position, the package container comprising a sheet of thermoplastic material formed into an envelope having a top opening and a bottom, a panel of bubble wrap material inserted into the envelope to form a first and a second pocket within the envelope, the first and second pockets each having a top opening corresponding to the top opening of the envelope, means for closing the top opening of the envelope to close the pockets, and a fusion line formed near the bottom of the envelope to form a section of the bubble wrap material between the bottom of the envelope and the fusion line.

2. The package container of claim 1 wherein the envelope has a front side and a back side and the first pocket is formed between the back side and the panel of bubble wrap material and the second pocket is formed between the front side and the panel of bubble wrap material.

3. The package container of claim 2 wherein the fusion line is formed between the front side and the panel of bubble wrap material.

4. The package container of claim 3 wherein the envelope further comprises a third pocket formed between the front side and the panel of bubble wrap material and adjacent to the second pocket.

5. The package container of claim 4 wherein the envelope further comprises a fourth pocket formed between the front side and the panel of bubble wrap material and adjacent to the third pocket.

6. The package container of claim 1 wherein the closing means comprises a flap which extends above the pockets with the flap having a band of adhesive and a strip of material placed over the band of adhesive, the strip of material being removable from the band of adhesive for adhering the flap to the envelope.

7. The package container of claim 1 further comprising a flap which extends from a side of the envelope with the flap having a band of adhesive and a strip of material placed over the band of adhesive, the strip of material being removable from the band of adhesive for adhering the flap to the envelope when the package container is rolled up.

8. The package container of claim 1 wherein the sheet of thermoplastic material is clear and allows any document inserted into the first pocket to be easily viewed.

9. A package container for storing and transporting at least one blood vial in a secured position, the package container comprising a sheet of thermoplastic material having a front side and a back side, the sheet being formed into the shape of an envelope having a top opening and a bottom, a panel of bubble wrap material inserted into the envelope to form a first pocket between the back side and the panel and a second pocket formed between the front side and the panel, the first and second pockets each having a top opening corresponding to the top opening of the envelope, the back side further having a flap portion extending above the envelope with the flap having a band of adhesive and a strip of material covering the band of adhesive, the strip of material being removable from the band of adhesive when the flap is positioned over the front side to close the top opening of the envelope, and a fusion line formed near the bottom of the envelope to form a section of the bubble wrap material between the fusion line and the bottom of the envelope.

10. The package container of claim 9 wherein the fusion line is formed between the front side and the panel of bubble wrap material.

11. The package container of claim 9 wherein the envelope further comprises a third pocket formed between the front side and the panel of bubble wrap material and adjacent to the second pocket.

12. The package container of claim 11 wherein the envelope further comprises a fourth pocket formed between the front side and the panel of bubble wrap material and adjacent to the third pocket.

13. The package container of claim 9 wherein the first pocket has a bottom and the fusion line forms the bottom of the first pocket.

14. The package container of claim 9 further comprising a flap which extends from a side of the envelope with the flap having a band of adhesive and a strip of material placed over the band of adhesive, the strip of material being removable from the band of adhesive for adhering the flap to the envelope when the package container is rolled up.

15. The package container of claim 9 wherein the sheet of thermoplastic material is clear and allows any document inserted into the first pocket to be easily viewed.

16. A package container for storing and transporting a medicine bottle in a secured position, the package container comprising a sheet of thermoplastic material having a front side and a back side formed into an envelope with the envelope having a top opening and a bottom, a panel of bubble wrap material inserted into the envelope to form a first pocket between the back side and the panel and a second pocket between the front side and the panel with the second pocket being further defined by a pair of fusion lines formed between the front side and the panel, the first and second pockets each having a top opening which corresponds to the top opening of the envelope, the back side further having a flap portion extending above the envelope with the flap portion having a band of adhesive and a strip of material covering the band of adhesive, the strip of material being removable from the band of adhesive when the flap is positioned over the front side to close the envelope, and a fusion line formed near the bottom of the envelope to form a section of bubble wrap material between the bottom of the envelope and the fusion line.

17. The package container of claim 16 wherein the fusion line is formed between the front side and the panel of bubble wrap material.

18. The package container of claim 17 wherein the envelope further comprises a flap which extends from a side of the envelope with the flap having a band of adhesive and a strip of material placed over the band of adhesive, the strip of material being removable from the band of adhesive for adhering the flap to the envelope when the package container is rolled up.

19. A package container for storing and transporting at least two blood vials in a secured position, the package container comprising a sheet of thermoplastic material having a front side and a back side, the sheet being formed into the shape of an envelope with the envelope having a top opening and a bottom, a second sheet of thermoplastic material inserted into the envelope to form a first pocket between the back side and the second sheet of thermoplastic material and a pair of pockets formed between the front side and the second sheet of thermoplastic material, the pair of pockets each having a top opening corresponding to the top opening of the envelope, the back side further having a flap portion extending above the envelope with the flap having a band of adhesive and a strip of material covering the band of adhesive, the strip of material being removable from the band of adhesive when the flap is positioned over the front side to close the envelope, and a fusion line formed near the bottom of the envelope to form a section of thermoplastic material between the bottom of the envelope and the fusion line.

20. The package container of claim 19 wherein the fusion line is formed between the front side and the second sheet of thermoplastic material at the bottom of the envelope.

* * * * *

UNITED STATES PATENT AND TRADEMARK OFFICE
CERTIFICATE OF CORRECTION

PATENT NO. : 5,791,476
DATED : August 11, 1998
INVENTOR(S) : Debra S. Stekloff

It is certified that error appears in the above-identified patent and that said Letters Patent is hereby corrected as shown below:

Column 5, line 41, "si de" should be --side--.

Signed and Sealed this

Twenty-seventh Day of October, 1998

Attest:

BRUCE LEHMAN

Attesting Officer

Commissioner of Patents and Trademarks